United States Patent [19]
Feinberg et al.

[11] Patent Number: 5,458,598
[45] Date of Patent: Oct. 17, 1995

[54] CUTTING AND COAGULATING FORCEPS

[75] Inventors: Marc Feinberg, Yardley, Pa.; Michael Seitzinger, Santa Fe, N.M.

[73] Assignee: Cabot Technology Corporation, Wilmington, Del.

[21] Appl. No.: 160,213

[22] Filed: Dec. 2, 1993

[51] Int. Cl.⁶ .................................................. A61B 17/39
[52] U.S. Cl. .................. 606/52; 606/51; 606/50; 606/205
[58] Field of Search ........................ 606/41, 42, 45–52, 606/205–208

[56] References Cited

U.S. PATENT DOCUMENTS

| | | |
|---|---|---|
| 2,002,594 | 5/1935 | Wappler et al. . |
| 2,004,559 | 6/1935 | Wappler et al. . |
| 2,028,635 | 1/1936 | Wappler . |
| 2,031,682 | 2/1936 | Wappler et al. . |
| 2,032,860 | 3/1936 | Wappler et al. . |
| 2,056,377 | 10/1936 | Wappler . |
| 2,068,721 | 1/1937 | Wappler et al. . |
| 3,875,945 | 4/1975 | Friedman . |
| 3,938,527 | 2/1976 | Rioux et al. . |
| 4,003,380 | 1/1977 | Wein . |
| 4,005,714 | 2/1977 | Hilterbrandt ............................ 606/51 |
| 4,016,881 | 4/1977 | Rioux et al. . |
| 4,057,063 | 11/1977 | Gieles et al. . |
| 4,114,623 | 9/1978 | Meinke et al. . |
| 4,209,018 | 6/1980 | Meinke et al. . |
| 4,311,451 | 1/1982 | Esty et al. . |
| 4,418,692 | 12/1983 | Guay . |
| 4,655,216 | 4/1987 | Tischer . |
| 4,671,274 | 6/1987 | Sorochenko . |
| 4,674,498 | 6/1987 | Stasz . |
| 4,802,476 | 2/1989 | Noerenberg et al. . |
| 4,862,889 | 9/1989 | Feucht . |
| 4,898,169 | 2/1990 | Norman et al. . |
| 4,936,842 | 6/1990 | D'Amelio et al. . |
| 4,976,711 | 12/1990 | Parins et al. . |
| 4,985,030 | 1/1991 | Melzer et al. . |
| 5,007,908 | 4/1991 | Rydell . |
| 5,013,312 | 5/1991 | Parins et al. . |
| 5,026,371 | 6/1991 | Rydell et al. . |
| 5,035,696 | 7/1991 | Rydell . |
| 5,047,026 | 9/1991 | Rydell . |
| 5,047,027 | 9/1991 | Rydell . |
| 5,057,107 | 10/1991 | Parins et al. . |
| 5,071,419 | 12/1991 | Rydell et al. . |
| 5,078,717 | 1/1992 | Parins et al. . |
| 5,083,565 | 1/1992 | Parins . |
| 5,085,659 | 2/1992 | Rydell . |
| 5,098,431 | 3/1992 | Rydell . |
| 5,125,928 | 6/1992 | Parins et al. . |
| 5,147,357 | 9/1992 | Rose et al. . |
| 5,158,561 | 11/0992 | Rydell et al. . |
| 5,163,942 | 11/1992 | Rydell . |
| 5,171,255 | 12/1992 | Rydell . |
| 5,171,311 | 12/1992 | Rydell et al. . |
| 5,190,541 | 3/1993 | Abele et al. ............................ 606/50 |
| 5,192,280 | 3/1993 | Parins . |
| 5,197,963 | 3/1993 | Parins . |
| 5,197,964 | 3/1993 | Parins . |
| 5,201,732 | 4/1993 | Parins et al. . |
| 5,217,458 | 6/1993 | Parins . |
| 5,217,460 | 6/1993 | Knoepfler . |
| 5,250,047 | 10/1993 | Rydell . |
| 5,258,006 | 11/1993 | Rydell et al. . |
| 5,267,998 | 12/1993 | Hagen ....................................... 606/49 |

Primary Examiner—Stephen C. Pellegrino
Assistant Examiner—Michael Peffley
Attorney, Agent, or Firm—Shoemaker and Mattare, Ltd.

[57] ABSTRACT

A cutting and coagulating forceps includes a housing with a protruding barrel, a pair of electrocautery jaws which are closed by camming contact with the mouth of the barrel when the jaws are retracted, and an independently sliding blade which passes between the jaws. The jaws are opened by squeezing a trigger, and the blade is advanced by pressing a lever with the thumb. Forward blade movement is limited by a stop whose position is a function of jaw position, so that the blade cannot strike the jaws, yet always can travel short of contact with the tips of the jaws.

15 Claims, 3 Drawing Sheets

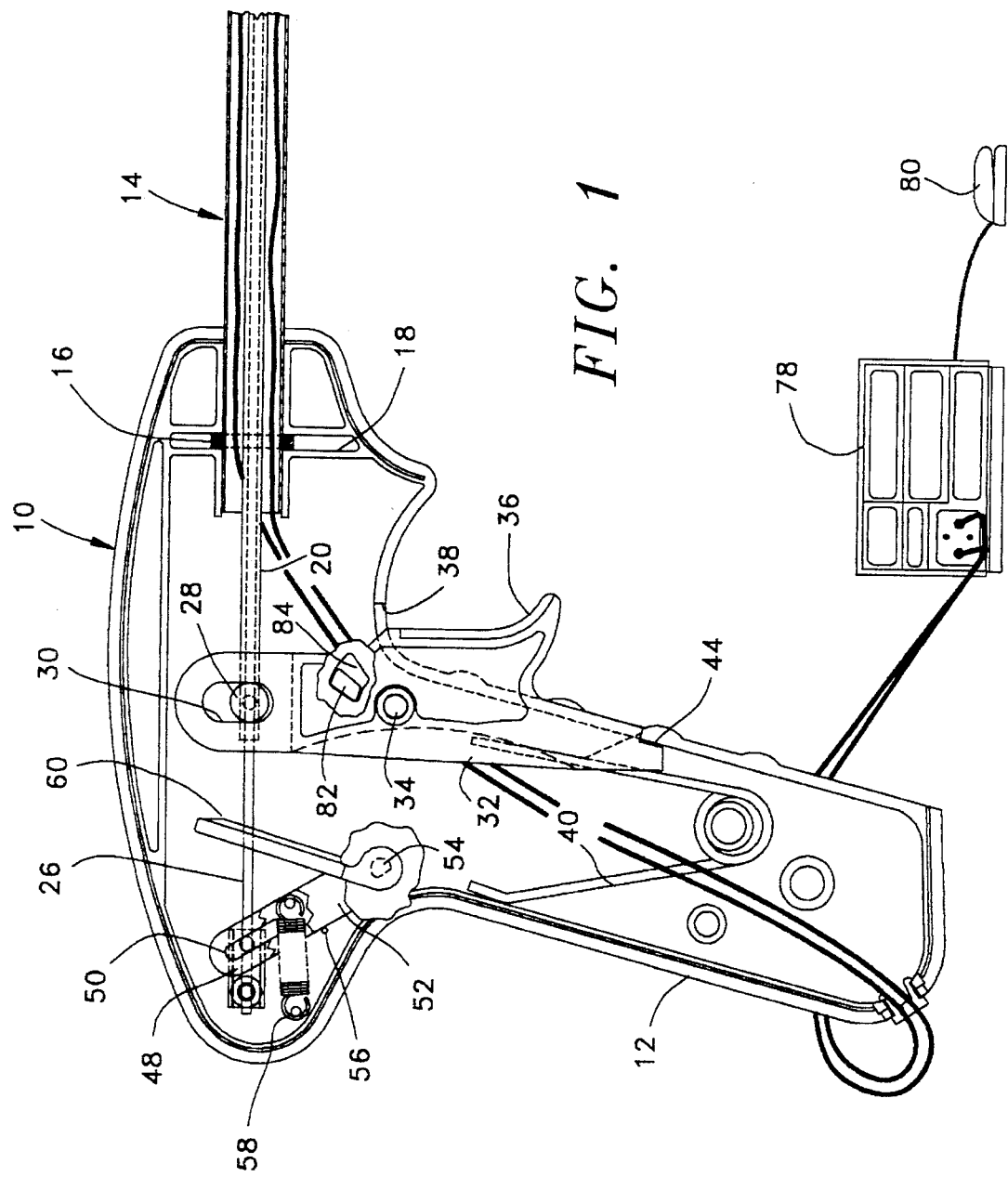

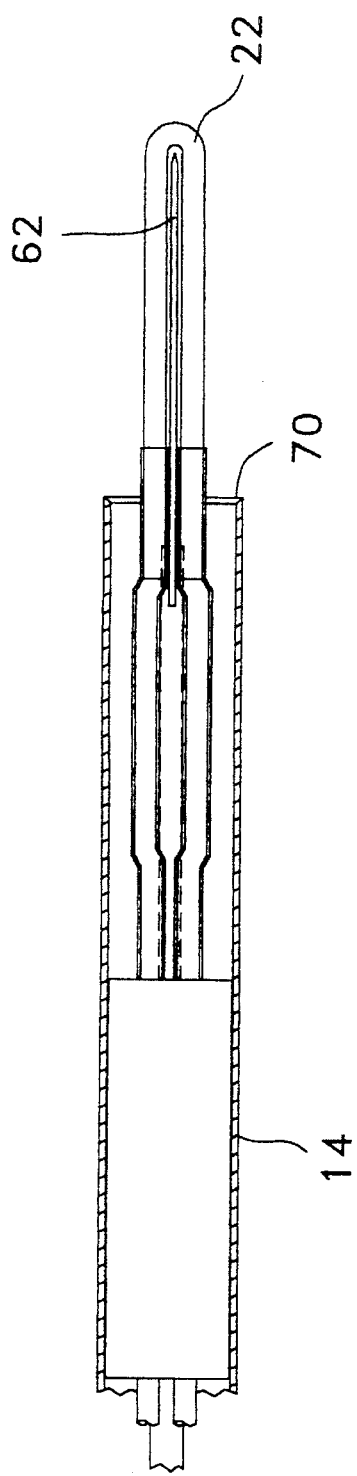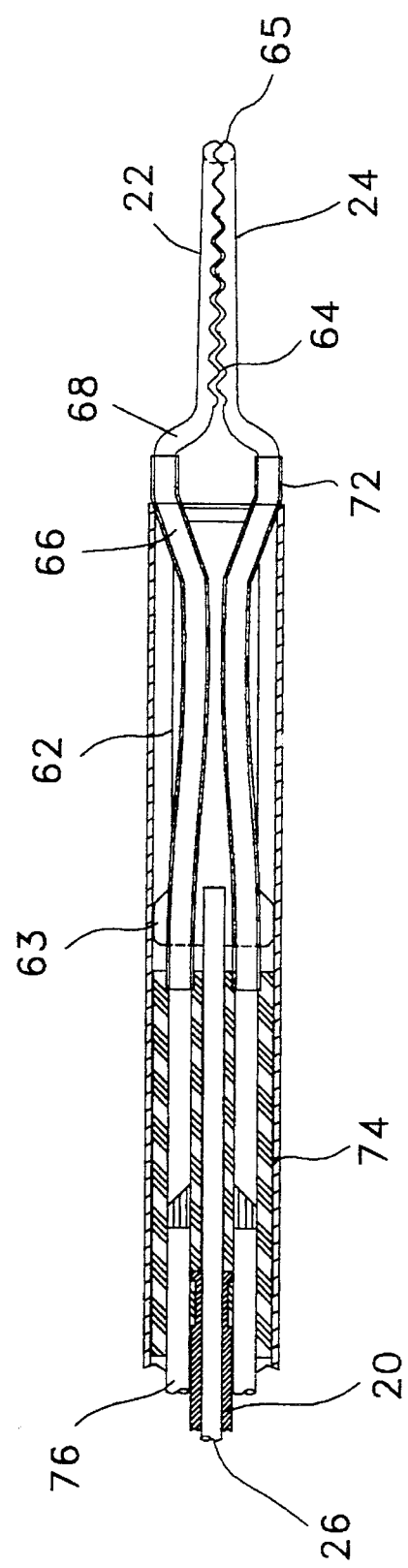

5,458,598

CUTTING AND COAGULATING FORCEPS

BACKGROUND OF THE INVENTION

This invention relates generally to surgical instruments and, more particularly, to a cutting and coagulating forceps.

Electrosurgery involves the application of electrical energy to tissues. Water is evaporated from tissues during electrosurgery, and with proper control of the intensity, frequency and duration of the applied energy, a surgeon can either coagulate or cut tissues.

A number of expired patents disclose electrocautery forceps having a pair of U-shaped jaws and a cutting wire which is advanced between the arms of the jaws to cut tissue clamped between them. A more recent U.S. Pat. No. 5,258,006, discloses an electrosurgical bipolar forceps having a pair of jaws which grasp and coagulate tissues, but not a cutting blade. The jaws are operated by a camming action produced when the jaws are moved along the tool by operating a lever on the tool body.

In the present invention, a purely mechanical shielded cutting blade is employed, in conjunction with bipolar coagulating jaws. Both the blade and the jaws are independently movable along the axis of the tool. A high frequency voltage is applied across the opposed jaws after they have grasped a tube, ligament, or other tissue, to coagulate the tissue; once coagulated, the tissue is then mechanically cut by advancing the blade.

To enable the surgeon to cut completely through tissue clamped by the jaws, the blade must not travel beyond the coagulated area; otherwise, bleeding will occur. Ideally, the blade should have as much travel as possible within the jaws, but the blade must never actually contact the jaws, so a stop has been provided to limit forward blade motion. With this invention, the stop is movable, and affixed to the jaw actuating lever, so that regardless the location of the jaws, the blade is always stopped short of contact with the jaw tips. Thus, the blade stop moves to compensate for changes in jaw position.

SUMMARY OF THE INVENTION

An object of the invention is to prevent contact between a movable cutting blade and a pair of axially movable electrosurgical forceps jaws, while otherwise maximizing blade movement.

Another object of the invention is to enable a surgeon to move coagulating jaws and an associated cutting blade independently, without having to worry about interference between the blade and the jaws.

These and other objects are attained by a cutting and coagulating forceps including a handgrip-shaped housing with a protruding barrel, a pair of electrocautery jaws which are closed by interference with the mouth of the barrel when the jaws are retracted, and an independently sliding blade that passes between the jaws. The jaws are opened by squeezing a trigger, and the blade is advanced by pressing a lever with the thumb. Forward blade movement is limited by a stop whose position is a function of jaw position, so that the blade cannot strike the jaws.

BRIEF DESCRIPTION OF THE DRAWINGS

In the accompanying drawings:

FIG. 1 is a view of a cutting and coagulating forceps, taken on a vertical plane substantially bisecting the device, showing the handle of the forceps and a rear portion of a barrel;

FIG. 2 is a sectional view, taken from the top, of the front portion of the barrel and jaws protruding therefrom, showing the cutting blade in its retracted position, FIG. 3 is a side sectional view thereof, but with the blade advanced.

DESCRIPTION OF THE PREFERRED EMBODIMENT

Figure 4:
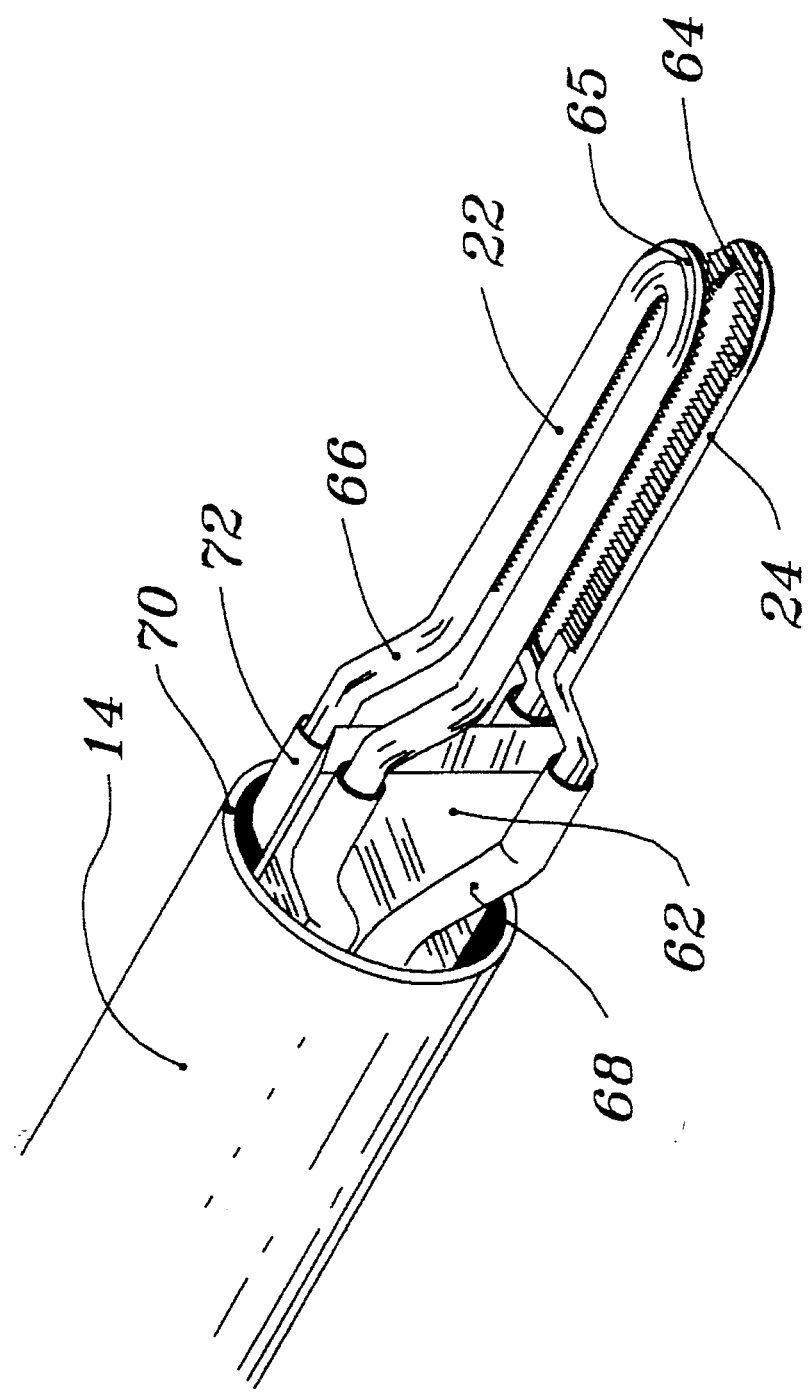
FIG. 4 is a perspective view of the distal end of the forceps.

A cutting and coagulating forceps embodying the invention includes a molded plastic housing 10 (FIG. 1) having a downwardly extending handle 12. A presently preferred material for the housing is produced by Monsanto under the trademark Lustran ABS. The housing is formed in substantially symmetrical halves joined on a vertical plane of symmetry "V". A tubular barrel 14 protrudes from the forward end of the housing, where it is retained between the halves by the combination of a ring 16 welded to the rear of the barrel and a corresponding annular groove 18 in the housing.

The item running coaxially through the barrel 14 is a small metal tube 20. It is connected at its forward or distal end (FIG. 2) by a plug described below to a pair of jaws 22,24, and can move along the axis of the barrel to move the jaws. Within the tube is a slender rod 26 that is axially movable independently of the tube.

The rearward (proximal) end of the tube 20 (FIG. 1) is secured by set screws to a clevis 28 confined within vertically extending slots 30 at the upper end of spaced arms of an actuating lever 32. The lever is supported within the housing by a pin 34, whose ends are supported by the housing. The lever is concealed, except for a trigger portion 36 that extends through a slot 38 at the forward side of the handle. When the trigger is squeezed toward the handle 12, it pivots the lever 32 in one direction (clockwise, when viewed from the right side of the tool as in FIG. 1) moving the clevis and tube forward. A hairpin-type torsion spring 40 engaging the bottom of the lever biases the lever counter-clockwise to a rest position defined by a stop 44 at the bottom of the lever. Clockwise movement of the lever is limited by interference between the pin 82 described below and the slot 84 through which it protrudes.

The rear end of the slender rod 26 is affixed to a clevis 48, having set screws for adjustment, that rides in a slot 50 at the upper end of an idler arm 52 within the housing, supported on a transverse pivot shaft 54. The idler arm is normally drawn rearward, against a stop pin 56 in the housing, by a tension spring 58. The pivot shaft extends from both sides of the housing. Symmetrical thumb levers 60 are installed on the pivot shaft's ends, outside the housing. The pivot shaft's ends are provided with flats, keys or non-circular cross-sections to lock them to the thumb levers. Pressing either thumb lever forward pivots the shaft and the idler arm, driving the rod 26 forward. Providing two thumb levers makes the device ambidextrous, but one could modify the device by omitting one of the levers omitted, if desired.

A cutting blade 62 (FIGS. 2–4) is affixed to the distal end of the rod 26. The blade has a sharp, square cutting edge at its forward end, and wings 63 at its rearward end that have a close sliding fit within the barrel. The rear edge of the blade is rigidly affixed to the forward end of the slender rod by welding, for example.

The coagulating jaws 22,24 extend beyond the barrel mouth 70 a variable distance, depending on the trigger pressure and the thickness and nature of any tissues captured between the jaws. Maximum jaw stroke is about 0.25 inch. Each jaw, which may perform a coagulation function, is formed from a bight of slightly flattened stainless steel wire, so that it has a "U" shape when viewed vertically, as in FIG. 3. The cutting blade is disposed within the 0.048 inch wide gaps between the arms of each "U", with the width of the blade extending vertically. As can be seen in FIG. 2, the blade has a sharp, square cutting edge facing forward, about even with the front end of the barrel when the blade is in its normal rest position (retracted). In this position, the blade is shielded by both the barrel and the jaw tips 65 to help prevent accidental cuts. The blade's maximum stroke is about one inch when the jaws are fully retracted, more when the jaws are extended.

The jaws have serrated mating surfaces 64, each comprising about ten teeth having a pitch of about 0.076 inch. The oblique faces of the teeth are at about 45° to the length of the jaws, and the teeth are arranged so that they mesh when the jaws close about a horizontal plane "H". One can see that the jaws converge at a slight angle toward the tip. The reason for the convergence is that, otherwise, the jaws would contact each other first at their proximal ends, closing the circuit and preventing current from reaching the tips.

The wires forming the jaws are bent so as to form what appears in FIGS. 2 and 4 as a bulge comprising proximal diverging segments 66 and distal converging segments 68. The bulge is larger than the barrel diameter, so that the diverging wire sections act as camming surfaces against the internally beveled mouth 70 of the barrel when the jaws are retracted.

The diverging segments 66 of the jaw wires are covered with a heat shrink electrical insulation material 72 which prevents electrical contact between the jaw wires and the barrel.

The proximal ends of the jaw wires are adhered within a cylindrical plastic plug 74 which electrically insulates the wires from one another, as well as from the barrel. The plug is molded as well around the distal end of the actuating tube 20 for the jaws, and thus serves both as a mechanical connector and an electrical isolator. The presently preferred material for the plug is a crystalline co-polyester amide known as Vectra LCP; however, other materials may prove suitable. The plug has a close sliding fit within the barrel, so that it functions as a dynamic seal to prevent loss of inflation gas from the surgical site. Within the plug, flexible conductors 76 are electrically connected to the proximal ends of the jaw wires. These conductors, shown diagrammatically, pass back through the barrel to the housing, down through the handle, and out through suitable connectors (not shown) to a power supply 78 controlled by a foot switch 80.

As mentioned, both the jaws and the blade can be independently reciprocated by the surgeon. Were the blade to be extended so far as to contact the looped end of the jaws, not only would be the blade edge be dulled, but also the blade would short the electrical path between the jaws. Thus, it is important to prevent overextension of the blade, and yet to maximize the stroke of the blade when the jaws are not retracted fully.

To prevent overextension, forward blade motion is controlled by a stop whose position is a function of jaw extension. This result is obtained by providing a movable stop for the thumb lever. The stop is in the form of a pin 82 protruding from the actuating lever 32, through a slot 84 in the housing 10. The flattened rear surface on the pin is engaged by the forward side of the thumb lever just before the blade contacts the jaw tips, regardless of jaw position. Inasmuch as the pin is above the trigger pivot, it moves in the same direction as (but less rapidly than) the jaws. The further forward the jaws are advanced by squeezing the trigger, the further forward the stop is, allowing the blade to be advanced farther. Conversely, the range of blade movement is reduced substantially when the trigger is released, to protect the blade and prevent unwanted electrical contact.

In use, a tissue is grasped between the jaws by first squeezing the trigger to open the jaws, then advancing the jaws over the tissue and releasing the trigger. The torsion spring pulls the jaws back into the mouth of the barrel, whose camming action drives the jaws together, clamping the tissue. Depending on the tissue thickness, the jaws remain partially open a greater or lesser amount. The surgeon then may depress the foot pedal 80, thereby impressing a high frequency voltage across the jaws, to coagulate the tissues. When the tissues have been sufficiently coagulated, the foot pedal is released, and the blade is then advanced by pressing one of the thumb levers forward. When the thumb lever is released, the tension spring retracts the blade, Finally, the tissue is released by squeezing the trigger.

Because the blade's forward stop position is automatically related to that of the jaws, it may be safely advanced until the stop pin is contacted, without fear of striking the jaws with the blade. The blade will thus remain sharp for at least the duration of the procedure, reducing costs and the need for spares.

Since the invention is subject to modifications and variations, it is intended that the foregoing description and the accompanying drawings shall be interpreted as illustrative of only one form of the invention, whose scope is to be measured by the following claims.

I claim:

1. A cutting and coagulating forceps comprising a housing, a tubular barrel protruding from a forward end of the housing, the barrel having an open mouth at its distal end, a pair of jaws partially protruding from the mouth of the barrel, and being movable in a direction parallel to the axis of the barrel, first manually operable means for moving the jaws parallel to the barrel axis, a cutting blade disposed between the jaws, and being movable along the axis of the barrel independently of the jaws, second manually operable means for advancing the blade along the barrel axis, and a movable stop fixed to the jaw moving means for limiting forward movement of the blade as a function of jaw movement so that the blade cannot strike the jaws, regardless of their position.

2. The invention of claim 1, wherein the jaws are electrically isolated from one another and from the cutting blade and the barrel, and further comprising a power supply for generating an alternating coagulating electrical current and conductors connecting said power supply to said jaws, wherein the jaws are electrically isolated from one another by a cylindrical plug molded around proximal ends of the jaws and secured to said jaw moving means, the cylindrical plug having a close sliding fit within the barrel, to provide a dynamic seal for preventing loss of inflation gas from a surgical site.

3. The invention of claim 1, wherein the jaw moving means comprises a lever pivotally mounted within the housing and having a trigger protruding from the housing whereby the lever can be pivoted in one direction by squeezing the trigger, a return spring for pivoting the lever in the opposite direction, and an elongated member connecting an upper end of the lever with said jaws.

4. The invention of claim 3, wherein the movable stop is affixed to said lever and moves in the same direction as the jaws when the trigger is squeezed.

5. The invention of claim 3, wherein the movable stop protrudes through a slot in the housing into the path of the thumb lever.

6. The invention of claim 1, wherein each jaw has a toothed surface facing the opposite jaw.

7. The invention of claim 6, wherein each toothed surface comprises a series of teeth which mesh with those of the opposite jaw when the jaws are closed.

8. The invention of claim 7, wherein the jaws converge at a slight angle toward their tips, so that they meet first at their tips as they close.

9. The invention of claim 7, wherein the teeth have a pitch of about 0.076 inch.

10. The invention of claim 7, wherein the teeth are substantially triangular in cross-section, having surfaces disposed at about 45° to the length of the jaws.

11. A cutting and coagulating forceps comprising a housing, a tubular barrel protruding from a forward end of the housing, the barrel having an open mouth at its distal end, a pair of jaws partially protruding from the mouth of the barrel, and being movable in a direction parallel to the axis of the barrel, means for moving the jaws parallel to the barrel axis, a cutting blade disposed between the jaws, and being movable along the axis of the barrel independently of the jaws, means for advancing the blade along the barrel axis, and a movable stop connected to the jaw moving means for limiting forward movement of the blade, and wherein the jaw moving means comprises a lever pivotally mounted within the housing and having a trigger protruding from the housing whereby the lever can be pivoted in one direction by squeezing the trigger, a return spring for pivoting the lever in the opposite direction, and an elongated member connecting an upper end of the lever with said jaws, and wherein the elongated member is a tube substantially coaxial within said barrel, and the blade moving means comprises at least one thumb lever pivotally supported on the housing, a rod affixed to said blade, and means linking the thumb lever to the rod.

12. The invention of claim 11, wherein the rod passes through said tube.

13. The invention of claim 11, wherein the linking means comprises a pivot shaft supporting said thumb lever, an arm within the housing connected to the pivot shaft, and a clevis connecting one end of the rod to the arm.

14. The invention of claim 13 comprising two said thumb levers, each being connected to a respective end of said pivot shaft.

15. The invention of claim 11, further comprising a return spring connected to said arm, for drawing said rod rearward.

* * * * *